(12) United States Patent
Bennett

(10) Patent No.: US 6,461,341 B1
(45) Date of Patent: Oct. 8, 2002

(54) ABSORPTION OF LIGHT BODILY DISCHARGES

(76) Inventor: Joseph H. Bennett, 1198 Navigator Dr. #28, Ventura, CA (US) 93001

( * ) Notice: Subject to any disclaimer, the term of this patent is extended or adjusted under 35 U.S.C. 154(b) by 73 days.

(21) Appl. No.: 09/746,910

(22) Filed: Dec. 23, 2000

(51) Int. Cl.⁷ ................................................. A61F 13/15
(52) U.S. Cl. .............. 604/385.18; 604/358; 604/385.01
(58) Field of Search ............................... 604/317–402, 604/385.01, 385.06, 385.18, 685.14, 358

(56) References Cited

U.S. PATENT DOCUMENTS

| | | | |
|---|---|---|---|
| 4,067,336 A | 1/1978 | Johnson | |
| 4,182,335 A | 1/1980 | Matrullo | |
| 4,484,919 A | 11/1984 | Sohn et al. | |
| 4,505,707 A | 3/1985 | Fenney | |
| 4,595,392 A | 6/1986 | Johnson et al. | |
| 4,946,454 A | 8/1990 | Schmidt | |
| 5,336,208 A | 8/1994 | Rosenbluth et al. | |
| 5,458,589 A | 10/1995 | Comin-DuMong | |
| 5,658,270 A | 8/1997 | Lichstein | |
| 6,258,074 B1 * | 7/2001 | Prazak ................... | 604/385.17 |

* cited by examiner

Primary Examiner—Jeanette Chapman
(74) Attorney, Agent, or Firm—Leo F. Costello

(57) ABSTRACT

A sanitary device for the absorption of light anal and vaginal/urethral discharges and a method for its use and disposal. The device includes a towelette and an attached string. The towelette is a thin, soft, dry, flexible sheet of absorbent paper material permeable to gas, absorbent of small amounts of moisture, and folded lengthwise into a pair of wings. The string is also soft and flexible and has ends attached to the towelette inside the wings and providing a relatively short outwardly extending loop. For anal use, the device is inserted between the buttocks and pinched and held by the sphincter muscle at the exit of the anal canal. For vaginal/urethral use, the device is inserted and fictionally held between the labial folds at the exit of the vagina. In either use, the loop of the string extends outwardly from the body and is accessible for convenient grasp by the wearer. The method involves grasping the towelette in one hand of the user and, with certain of the user's fingers inside the wings, pushing the towelette into the above-described anal or vaginal/urethral position, while minimizing direct hand-contact with these body regions. When neatly tucked into position, the device covers the anal or vaginal/urethral orifice with the wings flat against each other and in a position to intercept and filter light bodily discharges. The thin device is thus undetectable to most users and, when spent, is easily removed by grasping and pulling on the string and disposed of in an environmentally safe manner.

20 Claims, 4 Drawing Sheets

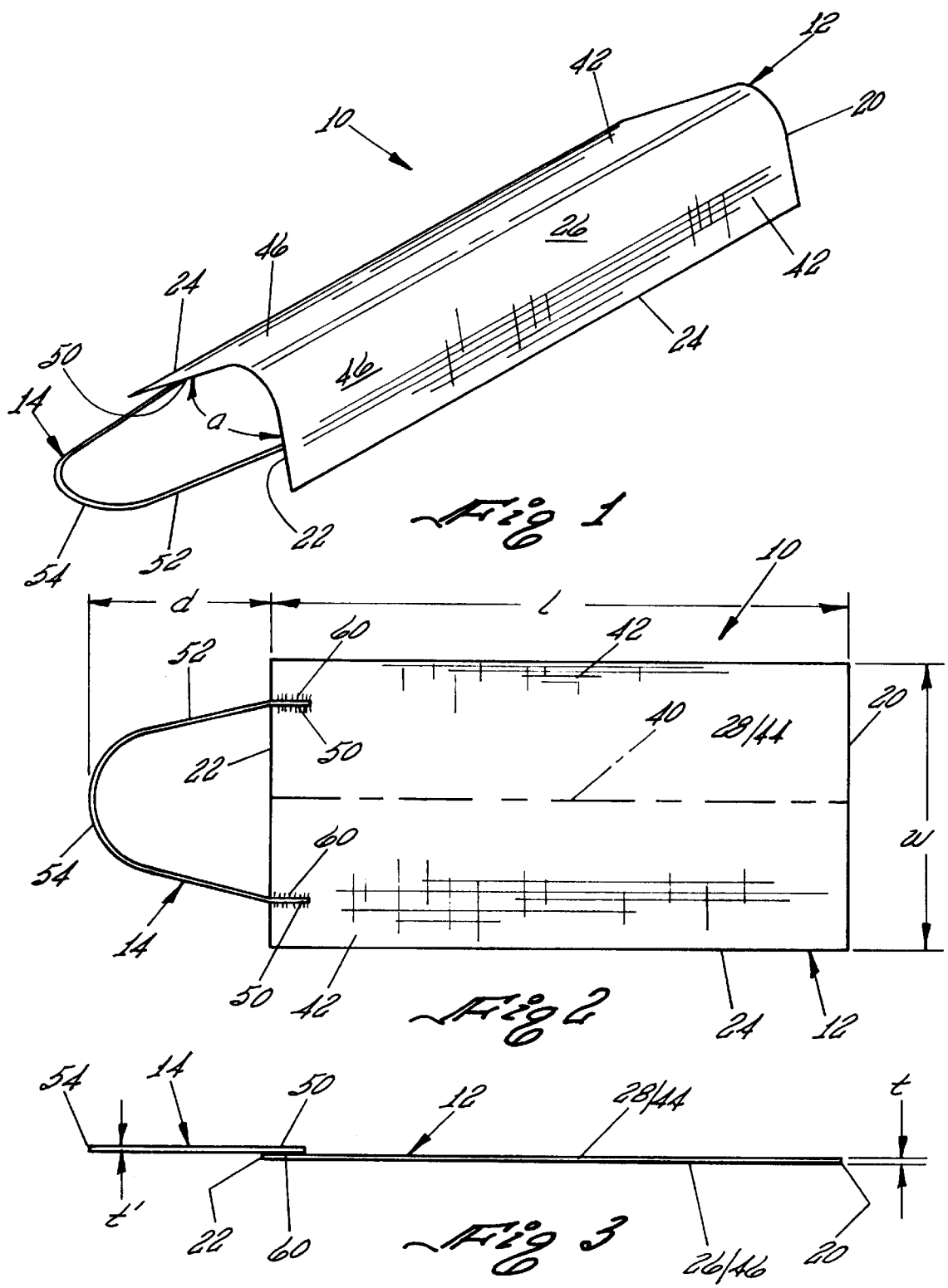

ABSORPTION OF LIGHT BODILY DISCHARGES

FIELD

The present invention pertains to the absorption of light bodily discharges and more particularly to a sanitary device for the absorption of light anal and vaginal/urethral discharges and to a method for its use and disposal.

BACKGROUND

It is well known that light amounts of anal and vaginal/urethral discharges require absorption for proper hygiene and personal comfort. The release of intestinal gas, for example, apart from normal bowel movements, may sometimes be accompanied by the release of small amounts of fecal matter, perhaps containing varying degrees of moisture. Such discharges may not be an occasion for a normal bowel movement nor of sufficient volume for such a movement, and they are usually unintentional and/or involuntary. Nevertheless, they are a rather common human occurrence, and although not often the subject of conversation, they usually require the attention, or at least get the attention, of the person affected. Some individuals, perhaps those of advanced age, may be more prone to such releases, but various foods or disorders of the digestive tract may be the cause in persons of any age.

Whatever the reason, such releases may result in great embarrassment and in addition may soil the person's clothing. If a clothing change is inconvenient or impractical, or perhaps not essential, the affected person must suffer the discomfort, either physical or mental, of the presence of the discharged matter on soiled undergarments. Even where no such matter is actually released, the person may not know this and may assume, albeit mistakenly, that the worst has happened.

Apart from such releases, undergarments may be soiled because of inadequate cleaning after a bowel movement. Even with reasonable cleaning, soiled streaking of underwear can occur simply due to bunching of the garment between the buttocks. Having to wear clothing soiled in the manner described thus leaves a person feeling unclean and uncomfortable. Presenting garments soiled in this manner for laundering is a further source of embarrassment.

The foregoing problems have been addressed in the Martrullo U.S. Pat. No. 4,182,335 and in patents cited therein. Martrullo discloses an anal filter including a layer of gauze and an overlying layer of fluffy cotton that is intentionally not compacted but is fluffed up into a thick layer and then folded over into dual layers prior to insertion. The patent states that such fluffiness is to provide for attachment of the device to a person and for gas pervasiveness. Although Matrullo provides no specific dimension for the thickness of the two layers, it may be inferred from his description and drawings that the thickness is about ¼" when unfolded prior to use on a person, and about ½" when folded (see FIG. 2 of the patent) for insertion and attachment to a person.

The Matrullo patent also refers to the Brown and Davis U.S. Pat. Nos. 3,570,489 and 3,881,485 and their disclosure of plugs that are intended to be pushed up the anal canal and even into the rectum when in operative position.

Whether or not the devices disclosed in the Matrullo, Brown or Davis patents would be effective to absorb fecal matter as described above is unknown to applicant. What is known is that to be of any use, any anal device must be worn. If a device is uncomfortable to the user, or is difficult, inconvenient, undesirable, or unsanitary to handle, it is unlikely to be worn. Devices that are of about ½" thick or even ¼" thick when placed between the buttocks, or that fit significantly into the anal canal or into the rectum are unlikely to be used since they are very likely to be uncomfortable. Apart from physical discomfort, the mere bulk and/or size of such a prior device makes the wearer conscious of its presence. Such devices are thus unacceptable as a solution to the above-described problem.

The absorption of light vaginal/urethral discharges is perhaps an even more universal problem or at least is given more general recognition. Various devices have long been known for absorbing such discharges including products commonly known as pantiliners. Although such products are generally useful for their intended function, they are typically limited to such function and are not useful for absorbing other bodily discharges, such as the anal discharges described above.

SUMMARY

A sanitary device for the absorption of light anal and vaginal/urethral discharges and a method for its use and disposal are provided. The device includes a towelette and an attached string. The towelette is a thin, soft, dry, flexible sheet of absorbent paper material permeable to gas, absorbent of small amounts of moisture, and folded lengthwise into a pair of wings. The string is also soft and flexible and has ends attached to the towelette inside the wings and providing a relatively short outwardly extending loop. For anal use, the device is inserted between the buttocks and pinched and held by the sphincter muscle at the exit of the anal canal. For vaginal/urethral use, the device is inserted and frictionally held between the labial folds at the exit of the vagina. In either use, the loop of the string extends outwardly from the body and is accessible for convenient grasp by the wearer. The method involves grasping the towelette in one hand of the user and, with certain of the user's fingers inside the wings, pushing the towelette into the above-described anal or vaginal/urethral position, while minimizing direct hand-contact with these body regions. When neatly tucked into position, the device covers the anal or vaginal/urethral orifice with the wings flat against each other and in a position to intercept and filter light bodily discharges. The thin device is thus undetectable to most users and, when spent, is easily removed by grasping and pulling on the string and disposed of in an environmentally safe manner.

An object of the present invention is to provide a sanitary device for the absorption of light anal and vaginal/urethral discharges and to a method for its use and disposal.

Another object is to provide a dual-purpose sanitary device that is alternatively usable for absorbing light anal or light vaginal/urethral discharges.

A further object is to absorb small amounts of fecal matter that may accompany the release of intestinal gas.

An additional object is to intercept and filter light anal or vaginal/urethral discharge before it contacts undergarments.

Another object is to avoid soiling undergarments either by fecal matter that is discharged when intestinal gas is released, and/or by such matter that has not been thoroughly cleaned from the anal region after a bowel movement or otherwise, and/or by vaginal/urethral discharges.

Yet a further object is to avoid the embarrassment of presenting garments soiled with fecal matter or vaginal/urethral discharges for laundering by someone other than the wearer.

A still further object is to give a person a feeling of cleanliness and well being notwithstanding the occurrence of anal or vaginal/urethral discharges or such possibility.

Another object is to provide a sanitary absorbent device that is undetectably worn on the user's body in covering relation to the anal or vaginal/urethral orifice instead of on the wearer's clothes.

Still another object is to absorb and filter light anal or vaginal/urethral discharges at the immediate exit of the anus or vagina.

Another object is to provide a sanitary anal or vaginal/urethral filtering device that is so thin as to be undetectable to most users and yet has sufficient absorbing qualities as to absorb light bodily discharges.

Yet another object is to provide a sanitary anal or vaginal/urethral device that is pinched and thereby held in place by the sphincter muscle at the exit of the anal canal or that is frictionally held by and between the labial folds of the vagina.

An additional object is to facilitate the insertion and removal of a sanitary device that absorbs light discharges from the anus or vagina.

A still further object is to insert a sanitary absorbent device into the anal or vaginal/urethral region with the fingers while minimizing direct contact of the fingers with these regions.

An added object is to be able to remove a sanitary absorbent device from its anal or vaginal/urethral position and to dispose or otherwise handle it without hand-contact with the anal or vaginal/urethral regions or with the portion of the device that is soiled.

Yet a further object is to provide a sanitary device that is soft and gentle on the wearer's skin, is non-toxic, and is disposable.

Another object is to provide sanitary, anal or vaginal/urethral absorbent devices that are easy and inexpensive to manufacture, package, and store, and to carry by the person using them.

These and other objects, features and advantages of the present invention will become apparent upon reference to the following description, accompanying drawings, and appended claims.

DESCRIPTION OF THE DRAWINGS

FIG. 1 is an isometric view of the sanitary device of the present invention including a towelette folded into two wings and an attached string extending outwardly from one end of the towelette, it being noted that FIG. 1 shows the device in its condition after having been folded and held in a stressed condition just to show its parts, and it being further noted that the towelette has sufficient resilience to return to a flat condition as shown in FIG. 2 when not being held in the FIG. 1 condition.

FIG. 2 is a full scale, bottom plan view of the subject device shown with the towelette unfolded and lying flat in its unstressed condition, indicating the longitudinal centerline of the eventual fold by a phantom line, and showing the attachments of the ends of the string to the inside of the wings of the towelette, it being noted that FIG. 2 shows the device in its condition for packaging, storing and carrying.

FIG. 3 is an edge view of the device as seen in FIG. 2 and thus with the towelette in unfolded, flat condition and the string extending outwardly from the towelette.

DETAILED DESCRIPTION

Figure 4:
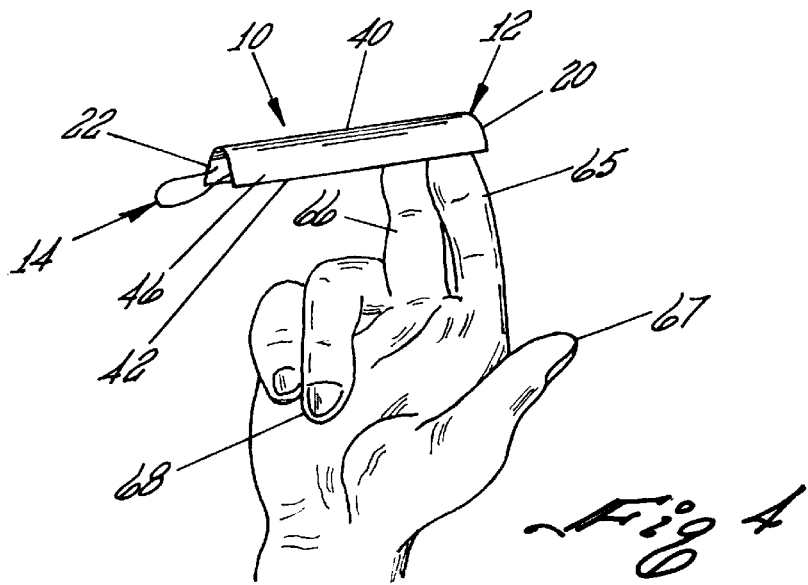
FIG. 4 is an isometric view of the device similar to but somewhat reduced from FIG. 1, showing the device after the towelette is folded and on a user's hand in preliminary position of preparation for bodily insertion, with the user's first and second fingers between the wings of the towelette, it being noted that in order to maintain the device in the FIG. 4 position, the user's thumb must be placed against the outside of the foreground wing of the towelette on the opposite side thereof from the first and second fingers but not shown that way here so as to avoid obscuring part of the device.
Figure 5:
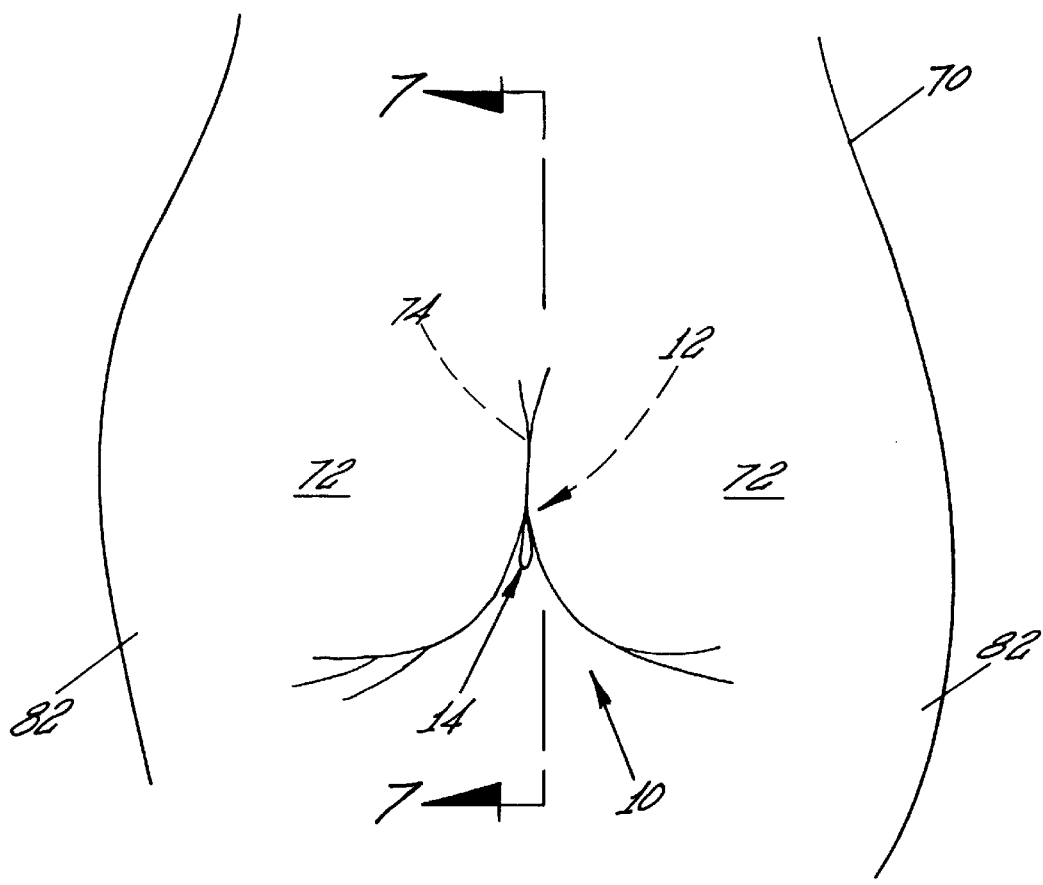
FIG. 5 is a fragmentary, rear elevational, schematic view of a portion of the human torso, either male or female, generally indicating the position of the subject device used as an anal sanitary device, it being noted that when the device is in place between the buttocks and pinched by the anal sphincter and over the anal orifice, the towelette is hidden from view but the string is visible and accessible, as seen in FIG. 5.

An embodiment of the sanitary device of the present invention is generally indicated by the number 10 in FIGS. 1–8. In general, the device includes a towelette 12 and a string 14 attached to the towelette. The towelette (FIGS. 1–3, especially) is a very thin, soft, dry, flexible, preferably rectangular, sheet or piece of absorbent paper material, of neutral color, e.g. white, permeable to gas and absorbent of small amounts of moisture, and yet has sufficient tensile strength when somewhat moist for the uses described herein. The towelette is preferably made from a disposable, single ply, white, wiper paper product made and sold by the Fort James Corporation of 1650 Lake Cook Road, Deerfield, Ill. 60015 under the trademark TASKMATE and described by that company as a disposable wiper not impregnated with chemicals or compounds. The towelette has a first end edge 20, a second end edge 22, side edges 24, an upper or outside surface 26, a lower or inside surface 28, a thickness t, a length l, and a width w. In the TASKMATE product preferably used for the towelette, the upper surface is smooth and the lower surface has a somewhat rougher, e.g., quilted, texture, desirable characteristics for these surfaces of the present invention, as will be seen.

Although the invention is not limited to any particular dimensions, the dimensions of the human torso naturally govern the preferred overall dimensions of the subject device. Preferred dimensions of the device are given herein to facilitate understanding of the device and its features and advantages, but it will be understood that these dimensions may be varied without departing from the principles of the present invention. Accordingly, the dimensions of a preferred embodiment of the subject device include a length l of about four inches and a width w of about two inches. Since an important feature of this subject invention is the thickness t, or more accurately the thinness, of the towelette, the preferred thickness t is a fraction of a millimeter.

Although flexible, the towelette 12 is made, sold, stored and carried in unfolded, flat or planar condition, as shown in FIGS. 2 and 3. Just prior to use, however, the towelette is folded, but preferably not creased, by the user longitudinally along a fold 40 represented by a phantom fold centerline in FIGS. 1 and 2 extending lengthwise of the towelette from the first end edge 20 to the second end edge 22 and in substantially parallel relation to and midway between the side edges 24. The fold divides the towelette into a pair of wings 42 that are initially held by the user at an angle "a" relative to each other as the device is being readied for insertion. When the towelette is inserted, as will be described, the wings are folded against each other. Each wing has an inside face 44 and an outside face 46 so that when the wings are folded against each other, the inside faces are in face-to-face contact. When the wings are in face-to-face contact, the total thickness of the device equals 2t. and w/2 equals about one inch. Because of the thinness of the towelette 12, however, the total thickness 2t is still less than one millimeter in the preferred embodiment.

Although prior to use and while in preparation for use, the towelette 12 is folded and held in folded condition by the user, it is to be understood that the fold 40 preferably does not create a permanent or sharp crease in the towelette, as above noted, whereby the wings of the towelette remain at the angle "a". In fact, the preferred TASKMATE paper product used as the towelette does not easily accept a permanent well-defined crease by mere hand-pressing along the centerline but tends to return to a planar condition when released from the user's grasp and to this degree may be considered as having resilience. The towelette is thus stressed by the user in the rounded condition of FIGS. 1 and 4 from which it would return to an unstressed flat or planar condition as shown in FIGS. 2 and 3 if released from the user's grasp. When inserted in the body, as will be described, and as the device is worn, the towelette may develop a more permanent crease, at least along a portion of the length of the fold 40.

The string 14 (FIGS. 1–6) is preferably a six-ply wrapping twine of poly/cotton fiber made and sold by Barbour Threads, Inc., a Coats Company, of 20 Blue Mountain Avenue, Anniston, Ala. 36201 under BIC No. 35280. The string is preferably of a neutral color, e.g. white, having a length from end-to-end of about four inches long and a diameter or thickness t' of about one millimeter. The string has end portions 50 that are attached to the inside and thus rougher faces 44 of the wings 42 adjacent to the intersection of the rear edge 22 and the side edges 24 of the towelette. As such, the string defines a loop 52 extending rearwardly from the towelette 12 to an apex 54 that, in the preferred dimensions given above and when the string loop extends outwardly from the towelette as seen in FIGS. 1–3, is at a distance d of about one and one-quarter of an inch from the end edge 22.

The end portions 50 of the string 14 (FIG. 2), which are preferably about five-sixteenths of an inch long in the preferred embodiment and are splayed, are attached to the inside faces 44 of the wings 42 of the towelette 12 by non-toxic glue or adhesive indicated at 60. The relative roughness of the inside surfaces of the wings and the splaying of the end portions of the string enhance the attachment of the string to the towelette 12 since the glue is more readily accepted both by the towelette and the string. A glue that is very suitable for the purposes of the subject invention is sold as Aleene's non-toxic tacky glue ASTM D-4236.

As will be seen in the description of the method, below, the smooth, upper or outer surface 26 of the towelette (i.e., the outer faces 46 of the wings 42) constitutes the anal or vaginal/urethral engaging surface or surfaces of the towelette, in contrast with the relatively rougher, lower or inner surface 28 (i.e., the inner faces 44 of the wings) that does not come in contact with these regions. As such, the end portions 50 of the string 14, which are raised relative to the lower or inner surface, does not rub or bear against the anal or vaginal/urethral areas, thereby avoiding a source of possible discomfort. Moreover, the effect of the wearer's body heat on the glued attachment of the end portions to the towelette is somewhat lessened by this separation.

It is also to be noted that prior to attachment to the towelette 12, the string 14 flexes in the well-known manner of a string of the type used herein and will hang straight down when held at one end if not otherwise supported. As attached to the towelette, however, the string does not droop as might be expected. In the short length used for the subject device 10 and as attached to the towelette, a measure of stiffness is imparted to the loop 52 so that it projects endwardly outwardly from the towelette at a slight downward angle, as seen in FIGS. 1 and 4. That is, because of the lightness of the string 14 and the body thereof, the distance d from the end edge 22 to the apex 54 of the loop 52, and the attachments 60 of the end portions 50 to the inside faces 44 of the towelette 12, the loop does not hang limp from the towelette when the towelette is held horizontal with the surface 26 facing upward. Rather, the loop declines endwardly outwardly from the towelette, as indicated in FIGS. 1 and 4, at an angle of from about ten degrees to about forty degrees. The loop maintains this position without any support other than its attachment to the towelette. Although the angle of decline is not critical, this self-supporting extension of the loop may facilitate handling of the device 10, as will be seen. Note that FIG. 3 is not intended to illustrate this self-supporting characteristic of the loop 52 since in FIG. 3, the string is intentionally fully stretched-out in a position that it would assume if the device were fully supported on a table or in a package of the devices, in order to illustrate the features of the device.

Method of Use

As stated, the subject sanitary device 10 is best sold, stored and carried in unfolded, flat or planar condition, as shown in FIGS. 2 and 3, since it has the thinnest profile in this condition. Normally, the devices would be sold in a package, not shown, of perhaps ten or more devices, for example, with the towelettes 12 all lying coincident and flat against each other, with the lower or inner surface of each device against the upper or outer surfaces of the adjacent device, and with the strings 14 extending outwardly. Such packaging may be visualized in FIGS. 2 and 3, although these figures show only a single device. In this way, the devices are compact, are generally preserved in their flat condition ready for proper folding, and may be carried in a pocket, handbag, or purse. The user can readily access a single device by opening the package, grasping the string loop 52 of the device selected, and pulling it away from the others in the package.

To use the device 10, the towelette 12 (FIGS. 1 and 4) is first folded along the fold centerline 40, as described above, with the wings 42 separated about at angle "a", as shown in FIGS. 1 and 4. As above stated, the subject device is a dual-purpose sanitary device alternatively usable for absorbing light anal or light vaginal/urethral discharges. The method of anal insertion will be described first, and for this purpose, reference is made to FIGS. 5–7 that include, in one or more of these views, schematic illustrations of a fragment of a user's torso or body 70, the buttocks 72, the anus 74, the anal canal 76, the anal orifice or exit 77 of the anal canal, the anal sphincter 78, the rectum 80, and the user's legs 82.

For right-handed anal insertion, the user initially holds the towelette (FIG. 4) at the string end 22 with the left hand, not shown, and then inserts the first and second fingers 65 and 66 of the right hand between the wings of the towelette intermediate the ends 20 and 22, either somewhat forwardly of the towelette, as shown in FIG. 4, or more centrally thereof than shown. Although not shown but easily visualized in FIG. 4, the right thumb 67 is then pressed against the outside face 46 of the foreground wing so as generally to sandwich this wing between the first and second fingers and the thumb. When thusly grasped in the right hand, the left hand is released, so that the device is ready for one-hand insertion. Held in this way, the string loop 52 projects rearwardly as preferred. It is to be noted, however, that some user's may prefer forward loop projection whereupon the non-string end 20 is initially held by the left hand, and the first and second fingers 65 and 66 of the right hand are inserted between the wings of the towelette intermediate the ends, as described above.

While holding the device 10 in the user's right hand as described and assuming rearward projection of the loop 52, there are two preferred methods of inserting the device 10 into the anal position in the user's body 70, one while seated and the other while standing. For the seated method, the user sits on the commode, not shown, causing the buttocks 72 to spread naturally and allowing the anal sphincter 78 to be in a closed position, slightly concave or domed upward. It may then be necessary to pull the sphincter slightly open, thereby relieving the normal constricting muscle pressure. The user then tilts over to the left, being supported on the commode by the left buttock. The folded sanitary device 10 is held in the user's right hand, as above described, with at least the first and second fingers 65 and 66 on the inside of the wings 42 and the thumb 67 on the outside of and against one wing, thereby maintaining a firm grasp on that wing and thus on the device, and with the string loop 52 pointing back.

Figure 7:
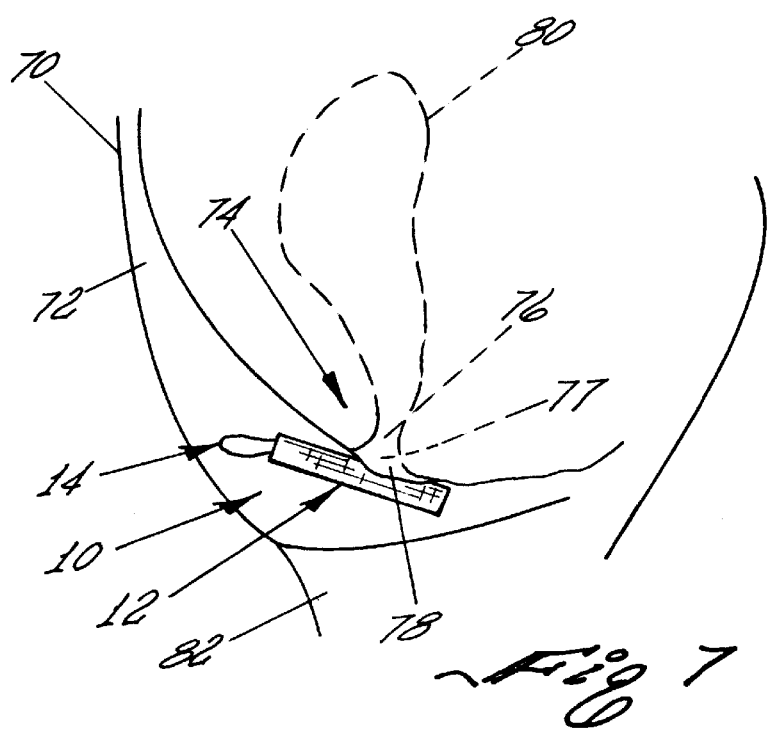
FIG. 7 is a vertical section taken generally along line 7—7 in FIG. 5.

At this point in the procedure, it is necessary to open the anal sphincter 78 even more and to slide the towelette 12 into the sphincter. The steps to accomplish these actions may be performed in various sequences and to some degree simultaneously, depending on the user's preferences. As one example, the device is brought into contact with the raised right buttock and slid along this buttock toward the anus 74, while at the same time releasing the thumb from the device as the towelette approaches the anal sphincter 78. The towelette is then brought into contact with the sphincter by only the user's two covered fingers 65 and 66. Using the heel of the right hand, slight pressure is applied to the right buttock 72 to open the anal sphincter 78 just enough to accept a small segment, perhaps as little as a few millimeters, of the towelette along the centerline of the fold 40. The fold is moved into the open sphincter intermediate the ends 20 and 22 of the towelette in covering relation to the anal orifice 77 and the anal canal 76, with the string loop 52 projecting rearwardly from the buttocks 72, outside of the body 70 and between the legs 82, as illustrated in FIG. 7. The heel pressure is then removed thereby allowing the sphincter to close and pinch the towelette in its preferred anal position, slightly rearwardly inclined, as shown in FIG. 7. For a moment, the user will very likely feel the device being held in place by the sphincter, as the heel pressure on the buttock is released. Experience has shown that after that brief sensation, the device will be essentially undetectable to most users.

For the standing method, and continuing to assume right-handed insertion and rearward projection of the loop 52, the user holds the device 10 in the right hand only, as above described. The user then bends forward, shifting the weight to the left leg 82, while slightly bending the knees for balance. At this point, the user's buttocks 72 are in positions generally equivalent to their described positions on the commode when raised on one buttock. Thus, the steps described above for the seated method may then be followed in the standing method to effect proper anal insertion.

It will be understood that left-handed insertion of the device 10 may be accomplished in a similar manner with just the left hand, albeit from the left side of the body 70.

By inserting the device in one of these ways, the user is assured that the device 10 is in place and will remain there all day if desired, resisting dislodgement due to such motion of the buttocks as occurs during walking, running, sitting, or the like. In this pinched, anal position, the towelette 12 totally covers the anal orifice or exit 77 of the anal canal 76, absorbs light discharge, and prevents such discharge from coming in contact with the user's underwear. Placing the sanitary device in the sphincter 78 by one of these methods, i.e., while the buttocks 72 are at extreme positions of separation and then allowing the device to be pinched in the sphincter, assures a positive hold on the device in its proper anal position where it is capable of intercepting, absorbing and filtering light anal discharges in the most efficient manner. Moreover, with either insertion method, the string loop 52 extends outwardly from the body 70, preferably rearwardly but possibly forwardly if desired, where it is readily accessible without appreciable body contact so as also to be essentially undetectable.

While being worn, if small amounts of fecal matter accompany the release of intestinal gas or if one's undergarment creeps into the cleavage of the buttocks 72, the towelette 12 intercepts and absorbs the matter and protects the wearer's undergarments from contact by the fecal matter. When wearing the subject device 10, the wearer may have less concern about soiling undergarments and the embarrassment of having them laundered. The wearer thus has a feeling of cleanliness and well being having the knowledge that fecal matter will be intercepted by the towelette but will not reach the undergarment.

Figure 8:
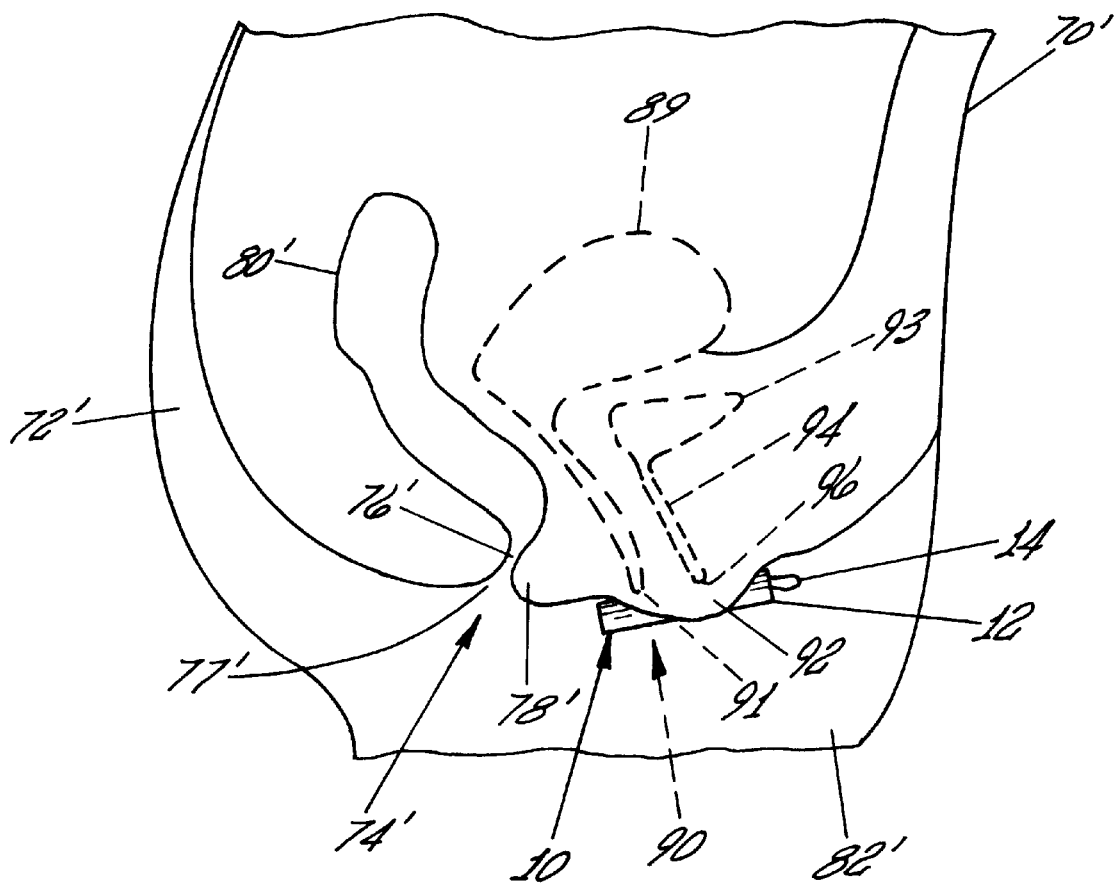
FIG. 8 is vertical section similar to FIG. 7 but showing the female torso with the subject device used as a vaginal/urethral sanitary device frictionally held between the labial folds of the vagina and in position covering the vaginal/urethral orifice.

For vaginal/urethral insertion, reference is made to FIG. 8 which schematically shows a fragment of a female torso or body 70', the buttocks 72', the anus 74', the anal canal 76', the anal orifice or exit 7' of the anal canal, the anal sphincter 78', the rectum 80', the legs 82', the uterus 89, the vagina 90, the vaginal entrance/exit or orifice 91, the labial folds or labia majora and minora 92, the bladder 93, the urethra or urethral canal 94, and the orifice or exit 96 of the urethral canal.

The sanitary device 10 is held in the left or right hand as above described for anal use, but the string loop 52 preferably projects forwardly. Again, the loop may project rearwardly if that is the user's personal preference. For forward projection, of course, the device is turned 180 degrees from its FIG. 4 position but held by the user's fingers in the same manner as above described. The device may be inserted into its vaginal/urethral position while sitting on the commode or standing. In either case, the labial folds 92, especially the inner labia minora, are pulled back with the left hand (for right-handed insertion), thereby exposing the vaginal/urethral orifice 91 and the urethral orifice 96. While holding the labial folds back with the left hand, the device 10 is inserted with the two fingers 65 and 66 of the user's right hand between the wings 42 and gently pushed into engagement with and in covering relation over the vaginal/urethral orifices. The intermediate portion of the fold 40 of the towelette 12 is thus placed over the vaginal/urethral orifices where it is capable of intercepting, absorbing and filtering light vaginal/urethral discharges. In this desired vaginal/urethral position, the towelette extends somewhat forwardly and rearwardly of the labial folds, and the loop 52 projects forwardly (or rearwardly as desired) out of the body and between the wearer's legs 82', readily accessible to the wearer.

After the device 10 has been placed in the described vaginal/urethral position, the labial folds 92 are released, causing them to move inwardly into engagement with the towelette 12 and hold the device in position by a friction fit. The labial folds 92 close and extend over a considerable area of the wings 42, thereby enhancing this friction fit. This is to be contrasted with the anal fit wherein the anal sphincter 78 may engage a much smaller area of the wings but does so with greater force resulting in the described pinching of the towelette 12. As with the anal use of the device, therefore, the user is assured that the device will remain in proper position all day if desired, resisting dislodgement and resulting embarrassment due to various bodily motions. Experience using the device in the manner described demonstrates that it is easy to use and comfortable in that it is undetectable, but most significantly, it absorbs light discharges from the vagina and thereby avoids staining of undergarments.

Figure 6:
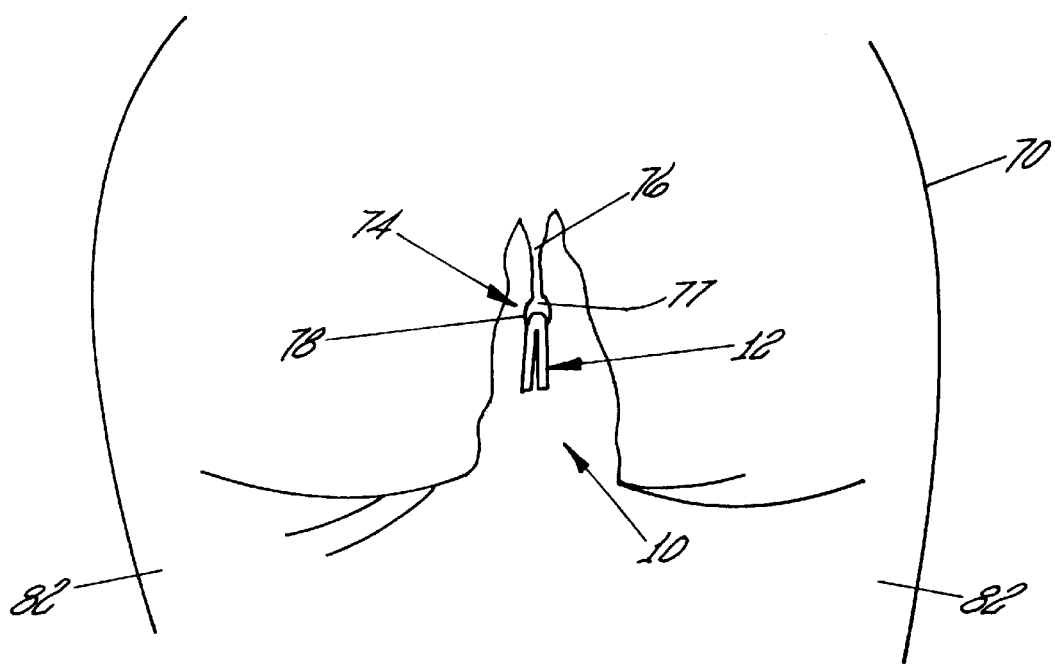
FIG. 6 is a schematic view similar to FIG. 5 but with the buttocks being broken away to show the sanitary device being pinched by the anal sphincter, it being noted that the size of the sphincter and the towelette, and particularly thickness of the towelette, are exaggerated for illustrative purposes.

It is important to recognize that with both uses, the undetectable characteristic of the device 10 when worn is achieved by the material used for the towelette 12 and the resulting thickness of the wings 42 (FIG. 3—also visualized in FIG. 6 although thickness dimensions in FIG. 6 are exaggerated so that details may be seen) when folded against each other, this thickness being less than about a millimeter in the preferred form. The thickness of the folded towelette 12 is thus less than the transverse dimension of the body tissue comprising the sphincter 78 when it is open. Of course, the thickness of the folded towelette is also less than the transverse dimension between the body tissue that comprise the labial folds 92 when they are opened. Notwithstanding this thinness, the towelette provides sufficient material to absorb light discharges at the point of discharge rather at the location of undergarments, as with many conventional sanitary devices. This feature thus overcomes problems with prior known sanitary devices that are so thick as to discourage their use.

Although the preferred method of wearing the device 10 for anal discharges is by allowing it to be pinched by the anal sphincter as above described, it will be understood that for both anal and vaginal/urethral uses, the primary purpose of the device is to intercept and absorb the discharge so that the device needs to be in a discharge-intercepting position, that is, in opposed, preferably contacting, relationship to the particular orifice 77, 77', 91, or 96 involved. Thus, anal pinching may be not be preferred, feasible, nor essential for all users to obtain the benefits of the present invention.

When it is desired to remove the device 10 (FIGS. 5–8), either for anal or vaginal/urethral use, the wearer grasps the loop 52 and pulls downwardly on it, causing the towelette 12 to slide outwardly from its bodily position. In the case of anal use, pulling downwardly on the loop will pull the towelette from its grasp by the anal sphincter 78 and thence from between the buttocks 72; it is desirable to pull downwardly especially while standing since the anal pinching of the towelette is so secure that the device may break with straight backward or upward pulling. In the case of vaginal/urethral use, pulling down on the loop will cause the towelette to slide out from its grasp by the labial folds 92. Sitting on the commode and opening the sphincter or the labial folds as in inserting the device may facilitate removal.

In each case, the towelette 12 has sufficient tensile strength and the glued attachments 60 of the string 14 to the towelette 12 are sufficient to resist tearing or separation of the string from the towelette, even when the towelette is lightly moistened by the discharged material. It is also to be noted that the attachments 60 are outside of the body when the device 10 is properly positioned either for anal or vaginal/urethral use whereby they are not subject to the body heat between the buttocks 72 or the labial folds 92 nor are these places 60 of attachment subject to moisture of the discharged material.

After removal from either the anal or vaginal/urethral region, and while holding the towelette 12 with the loop 52 of string 14, the used device is dropped into the commode or preferably into a refuse receptacle. The string thus allows the user to retrieve the device from the body and dispose of it without hand contact with the anal or vaginal/urethral regions or with the soiled, spent towelette.

Although a preferred embodiment of the present invention has been shown and described, various modifications, substitutions and equivalents may exist without departing from the spirit and scope of the invention. Accordingly, it is to be understood that the present invention has been disclosed by way of example and not by way of limitation.

What is claimed is:

1. A sanitary device adapted to be removably fitted over an orifice of the human body to intercept and absorb light discharges from such orifice, comprising:

a thin flexible towelette that is absorbent of light amounts of human bodily discharge, the towelette having opposite first and second end edges, opposite side edges, upper and lower surfaces, and being foldable along a longitudinally extending fold extending from the first end edge to the second end edge thereby dividing the towelette into a pair of wings extending away from the fold, the wings having opposed inwardly directed faces and outwardly directed faces, the towelette being adapted to be fitted over such an orifice with the fold directed toward the orifice, with the orifice located generally midway between the first and second end edges, and with the outwardly directed faces of the wings being engaged by the body parts adjacent to the orifice; and an elongated flexible loop having a pair of ends secured to the towelette, projecting outwardly from the first end edge and being adapted to project outside the user's body when the towelette is positioned against such an orifice of the body, the towelette having sufficient tensile strength and the string towelette attachments being sufficiently secure to resist tearing or breaking while being pulled by the loop from its position in the user's body even when partially moistened by light bodily discharge.

2. The device of claim 1,
wherein the towelette is less than one millimeter in thickness.

3. The device of claim 1,
wherein the towelette is made of soft paper.

4. The device of claim 1,
wherein the loop is made of string.

5. The device of claim 1,
wherein the ends of the loop are adhesively secured to the inwardly directed faces of the wings.

6. A sanitary device adapted to be removably fitted in the anal sphincter or between the labial folds of the human torso for absorbing light amounts of moist bodily discharge, comprising:

an elongated thin flexible dry rectangular paper towelette that is permeable to gas and absorbent of small amounts of light discharged matter, the towelette having opposite first and second end edges, opposite side edges, a smooth upper surface, a rougher lower surface, and being foldable along a longitudinally extending fold extending from the first end edge to the second end edge midway between the side edges and dividing the towelette into a pair of wings of substantially equal length and width, the wings having opposed inwardly facing lower faces and outwardly directed upper faces, the thickness of the towelette when folded being less than the transverse dimension of the anal sphincter when open and less than the transverse dimension between the labial folds when they are opened; and an elongated flexible string having a pair of ends secured in spaced relation to the lower faces of the wings respectively adjacent to the intersection of the rear end edge with the side edges and also having an endless loop extending rearwardly from the rear end edge, the towelette having sufficient tensile strength and the string towelette attachments being sufficiently secure to resist tearing or breaking while being pulled by the loop from its position in the user's body even when partially moistened by light bodily discharge.

7. The device of claim 6,
wherein the towelette is less than one millimeter in thickness when the wings are folded against each other.

8. The device of claim 6,
wherein the towelette is about four inches long by about two inches wide.

9. The device of claim 6,
wherein the string is attached to the towelette by nontoxic glue.

10. The device of claim 5,
wherein the string is made of poly/cotton.

11. A method of inserting and removing a sanitary device to and from body tissue adjacent to a body orifice from which discharge may occur, the device including a thin flexible towelette that is absorbent of light bodily discharge, the towelette having opposite first and second end edges, opposite side edges, upper and lower surfaces, and a flexible string secured to and projecting outwardly from the first end edge, comprising the steps of:

folding the towelette along a fold area extending from the first end edge to the second end edge thereby dividing the towelette into a pair of wings extending away from the fold area, the wings having opposed inwardly directed faces with an acute angle therebetween and outwardly directed faces, inserting one or more fingers between the wings and into contact with the fold area, pushing the towelette with said one or more fingers between such body tissue and into covering contact with a body orifice with the fold area directed toward the orifice, with the orifice located intermediate the end edges, with the outwardly directed upper faces against the body, and with the string projecting outside the body, and allowing the body tissue to engage the wings of the towelette.

12. The method of claim 11,
wherein the orifice is the anal orifice,
wherein the anal sphincter is opened, and
wherein the towelette is pushed into the open anal sphincter and is pinched by the sphincter when the anal sphincter closes.

13. The method of claim 12,
wherein the string has a pair of ends secured to the wings and a loop, and
wherein the loop extends outside the body.

14. The method of claim 13,
wherein the loop projects rearwardly from the body.

15. The method of claim 11,
wherein the orifice is the vaginal/urethral orifice,
wherein the labial folds are opened, and
wherein the towelette is pushed between the opened labial folds and is frictionally grasped by the labial folds when the folds are allowed to close.

16. The method of claim 15,
wherein the string has a pair of ends secured to the wings and a loop, and
wherein the loop extends outside the body.

17. The method of claim 16,
wherein the loop projects forwardly from the body.

18. The device of claim 11, including the further step of:
pulling downwardly on the string to remove the towelette from its position in the body.

19. A method of using a sanitary device to intercept and absorb light body discharges from the anus or the vagina/urethra, the device including an elongated, flexible, dry, rectangular paper towelette that is permeable to gas and absorbent of absorbing light body discharges, the towelette having a thickness of less than about one millimeter, opposite first and second end edges, opposite side edges, a smooth upper surface, a rougher lower surface, and a longitudinally extending fold extending from the first end edge to the second end edge midway between the side edges thereby dividing the towelette into a pair of uniformly sized wings extending away from the fold, the wings having opposed inwardly directed lower faces with an acute angle therebetween and outwardly directed smooth upper faces, and an elongated flexible string having a pair of splayed ends secured in spaced relation to the inwardly directed faces of the towelette respectively adjacent to the intersection of the rear end edge with the side edges and a loop extending rearwardly from the rear end edge, comprising the steps of:

grasping the towelette in one hand with two fingers of such hand between the wings transversely of the side edges intermediate the first and second end edges and into substantially right-angular engagement with the fold;

pushing the towelette into the anal sphincter for anal use or between the labial folds for vaginal/urethral use and into covering relation to the anal orifice or the vaginal/urethral orifices, as the case may be, by and with said fingers between the wings with the fold directed toward said orifice, with the orifice/orifices located intermediate the end edges, with the outwardly directed faces against the skin tissue around the orifice/orifices, and with the loop projecting from the towelette outside of the body;

sliding said fingers out from between the wings of the towelette while allowing the towelette to be grasped by and remain between said tissue adjacent to the respective orifice/orifices; and leaving the towelette between such tissue for a desired period of time wherein it is pinched by the sphincter or frictionally engaged by the labia.

20. The method of claim 19, including the further steps of:
pulling downwardly on the loop to remove the towelette from the body.

* * * * *